US00PP14790P2

(12) United States Plant Patent
Smith et al.

(10) Patent No.: US PP14,790 P2
(45) Date of Patent: May 18, 2004

(54) COLEUS PLANT NAMED 'SEDONA'

(50) Latin Name: *Coleus×hybrida*
Varietal Denomination: Sedona

(75) Inventors: Tom Smith, Carleton, MI (US); Michael R. Heulitt, Carleton, MI (US); Sandra Metzger, LaSalle, MI (US); Debbie Avery, Newport, MI (US)

(73) Assignee: Four Star GreenHouse, Carlton, MI (US)

( * ) Notice: Subject to any disclaimer, the term of this patent is extended or adjusted under 35 U.S.C. 154(b) by 0 days.

(21) Appl. No.: 10/452,081

(22) Filed: Jun. 2, 2003

(51) Int. Cl.[7] ..... A01H 5/00
(52) U.S. Cl. ..... Plt./373
(58) Field of Search ..... Plt./373

*Primary Examiner*—Bruce R. Campell
*Assistant Examiner*—June Hwu
(74) *Attorney, Agent, or Firm*—C. A. Whealy

(57) ABSTRACT

A new and distinct cultivar of Coleus plant named 'Sedona', characterized by its upright, outwardly spreading and mounded plant habit; vigorous growth habit; and red purple, orange and pale green tri-colored leaves.

1 Drawing Sheet

Botanical classification/cultivar denomination: *Coleus× hybrida* cultivar Sedona.

BACKGROUND OF THE INVENTION

The present Invention relates to a new and distinct cultivar of Coleus plant, botanically known as *Coleus×hybrida*, and hereinafter referred to by the cultivar name Sedona.

The new Coleus is a naturally-occurring whole plant mutation of the *Coleus frutescens* cultivar Freckles, not patented. The new Coleus was discovered and selected by the Inventors as a single plant within a population of plants of the cultivar Freckles in a controlled environment in Carlton, Mich. in October, 2001. The new Coleus was selected on the basis of its unique leaf coloration.

Asexual reproduction of the new cultivar by terminal cuttings taken in a controlled environment in Carlton, Mich. since October, 2001, has shown that the unique features of this new Coleus are stable and reproduced true to type in successive generations.

SUMMARY OF THE INVENTION

Plants of the cultivar Sedona have not been observed under all possible environmental conditions. The phenotype may vary somewhat with variations in environment such as temperature and light intensity without, however, any variance in genotype.

The following traits have been repeatedly observed and are determined to be the unique characteristics of 'Sedona'. These characteristics in combination distinguish 'Sedona' as a new and distinct Coleus cultivar:

1. Upright, outwardly spreading and mounded plant habit.
2. Vigorous growth habit.
3. Red purple, orange and pale green tri-colored leaves.

Plants of the new Coleus are most similar to plants of the parent, the cultivar Freckles. However, plants of the new Coleus differ from plants of the cultivar Freckles in the following characteristics:

1. Plants of the new Coleus are more vigorous, larger and grow faster than plants of the cultivar Freckles.

2. Plants of the new Coleus are more freely branching than plants of the cultivar Freckles.
3. Plants of the new Coleus have larger leaves than plants of the cultivar Freckles.
4. Plants of the new Coleus and the cultivar Freckles differ in leaf coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Coleus.

The photograph at the top of the sheet comprises a side perspective view of typical plant of 'Sedona' grown in a container.

The photograph at the bottom of the sheet side is a side perspective view of a typical plant of the parent, the cultivar Freckles.

DETAILED BOTANICAL DESCRIPTION

The cultivar Sedona has not been observed under all possible environmental conditions. The phenotype may vary somewhat with variations in environment such as temperature and light intensity without, however, any variance in genotype.

The aforementioned photographs, following observations and measurements describe plants grown in a fiberglass-covered greenhouse in Carlton, Mich. and under conditions which approximate commercial production cultural and environmental conditions. Plants were about 10 weeks from rooted cuttings and were grown in 15-cm containers. During the production of the plants, day temperatures averaged 19° C., night temperatures averaged 20° C. and light levels ranged from 2,500 to 8,000 footcandles.

In the following description, color references are made to The Royal Horticultural Society Colour Chart, 2001 Edition, except where general terms of ordinary dictionary significance are used.

Botanical classification: *Coleus×hybrida* cultivar Sedona.

Parentage: Naturally-occurring whole plant mutation of *Coleus×hybrida* cultivar Freckles, not patented.

Propagation:

*Type cutting.*—Terminal cuttings.

*Time to initiate roots.*—About 5 to 7 days at 19° C.

*Time to develop roots.*—About 28 days at 19° C.

*Root description.*—Fibrous; moderately thick; greyed-white, 156B, in color.

*Rooting habit.*—Freely branching.

Plant description:

*Form.*—Annual flowering plant; upright, outwardly spreading and mounded. Vigorous growth habit; moderate growth rate.

*Plant height.*—About 60 to 75 cm.

*Plant diameter.*—About 50 to 60 cm.

*Branching habit.*—Freely branching with potentially two lateral branches forming at every node.

*Lateral branches.*—Length: About 10 cm. Diameter: About 2 to 5 mm. Internode length: About 2 cm. Shape, in cross-section: Squarish. Strength: Moderately strong to strong. Texture: Slightly pubescent. Color: 151A with random spots and streaks, 70A.

*Foliage description.*—Arrangement: Opposite; simple. Length: About 7 cm. Width: About 5.5 cm. Shape: Ovate. Apex: Acute. Base: Truncate. Margin: Crenate. Texture, upper surface: Glabrous; rugose. Texture, lower surface: Slightly pubescent; rugose. Venation pattern: Pinnate. Color: Developing foliage, upper surface: N167B; towards base, 59A. Developing foliage, lower surface: 59A; venation, 151A. Fully expanded foliage, upper surface: 151A overlain with 24B and towards the base, 59C; venation, 58A. Fully expanded foliage, lower surface: 59B; venation, 151A. Petiole length: About 3.5 cm. Petiole diameter: About 3 mm. Petiole color: 151A.

Flower description: Flower development has not been observed.

Disease/pest resistance: Plants of the new Coleus have not been noted to be resistant to pathogens or pests common to Coleus.

Temperature tolerance: Plants of the new Coleus have been observed to tolerate temperatures from 2 to more than 35° C.

It is claimed:

1. A new and distinct cultivar of Coleus plant named 'Sedona', as illustrated and described.

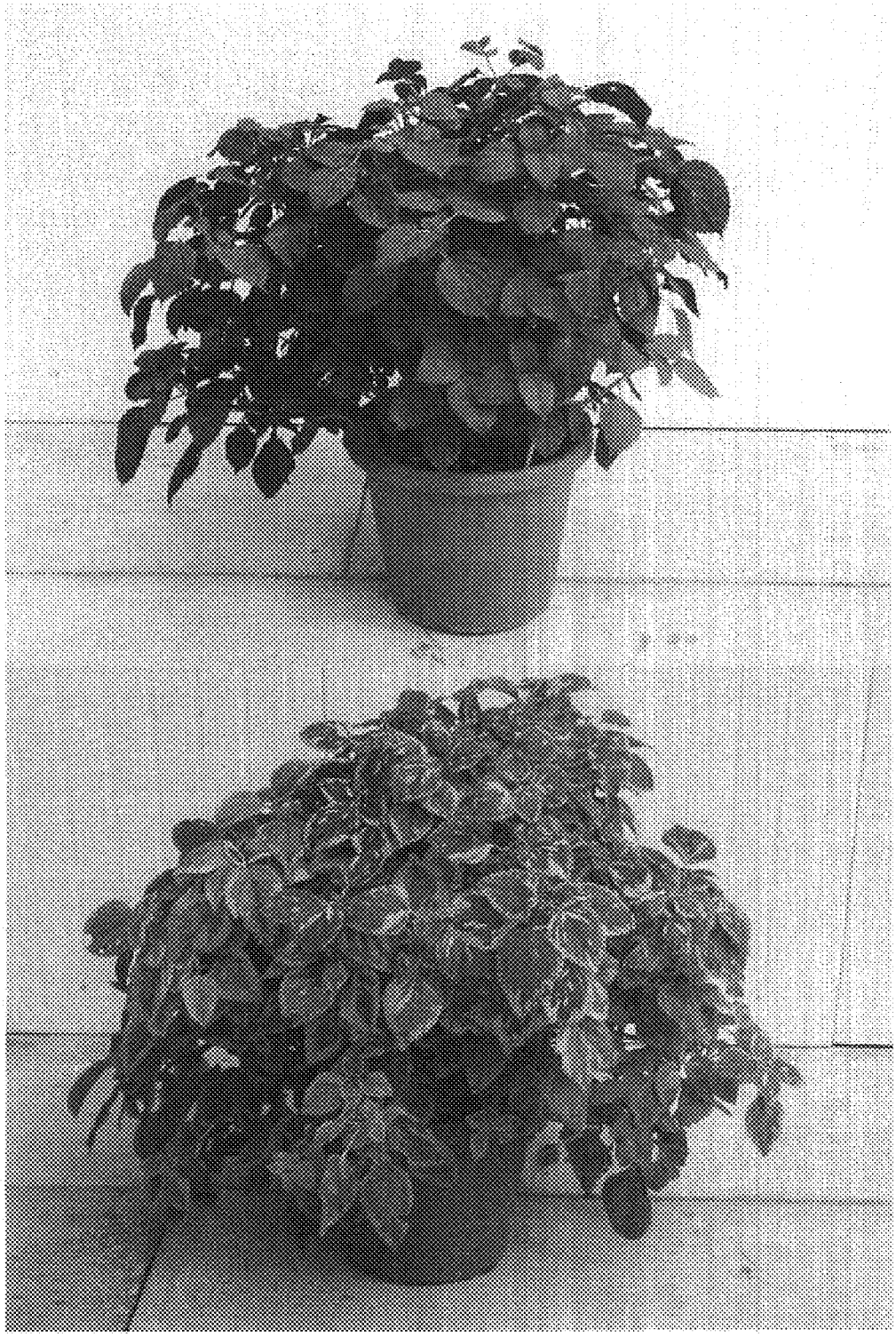

* * * * *